United States Patent [19]

Kleinwolterink

[11] 4,290,423

[45] Sep. 22, 1981

[54] PARAPLEGIC STAND HAVING A LIFT MECHANISM

[75] Inventor: Henry Kleinwolterink, Sheldon, Iowa

[73] Assignee: Main-Tainer Corporation, Sheldon, Iowa

[21] Appl. No.: 143,839

[22] Filed: Apr. 25, 1980

[51] Int. Cl.³ .................... A61F 3/00

[52] U.S. Cl. .................... 128/80 G

[58] Field of Search ................ 128/80 R, 80 G, 25 R; 280/79.3, 219, 220; 5/81 R

[56] References Cited

U.S. PATENT DOCUMENTS

| | | | |
|---|---|---|---|
| Re. 28,103 | 9/1974 | Schwartz et al. | 128/25 R |
| 3,958,568 | 5/1976 | Gaddy | 128/80 G |
| 4,029,089 | 6/1977 | Mulholland | 128/80 G |

FOREIGN PATENT DOCUMENTS

| | | | |
|---|---|---|---|
| 2749146 | 5/1978 | Fed. Rep. of Germany | 128/80 G |
| 2414911 | 8/1978 | France | 128/80 G |

*Primary Examiner*—John D. Yasko

*Attorney, Agent, or Firm*—Lowe, Kokjer, Kircher, Wharton & Bowman

[57] ABSTRACT

A stand device which includes a lift mechanism for raising paraplegic patients from a wheelchair to a standing position. The stand is mounted on caster wheels and includes a platform on which the feet of the patient are received. The lift mechanism includes a pair of electric actuators and a linkage which raises and lowers a pair of lift arms upon extension and retraction of the actuators. The lift arms carry a sling which is drawn behind the patient to lift him to a standing position on the platform when the actuators are extended.

9 Claims, 4 Drawing Figures

PARAPLEGIC STAND HAVING A LIFT MECHANISM

BACKGROUND AND SUMMARY OF THE INVENTION

This invention relates generally to a stand for supporting a paraplegic patient in an upright position. More specifically, the invention pertains to a stand which is equipped with a lift mechanism for raising the patient to a standing position.

It has long been known that significant therapeutic benefits are obtained when paraplegic patients periodically stand in an upright posture. For exaple, the patient exercises muscles that are only minimally used in the sitting position, circulation is increased, bladder pressure is increased, spasms and muscular tension are decreased, and the risk of pressure sores is decreased when the patient assumes a standing position. Also, the paraplegic patient often benefits psychologically if he or she is able to stand and move about.

U.S. Pat. No. 4,111,445 discloses one type of stand device that has been used by paraplegics to assist them in standing. Although this type of device functions well for many patients, it is not entirely satisfactory in all respects. Perhaps the most significant drawback is that considerable effort is required for the patient to pull himself up out of his wheel chair to a standing position, and this effort is beyond the physical capability of a large number of paraplegics. In addition, once the patient has assumed a standing position, straps or the like must be drawn around him and fastened in order to provide the necessary support.

It is the primary object of the present invention to provide an improved stand device for supporting a paraplegic patient in a standing position, which device includes a lift mechanism that operates to raise the patient from a wheel chair to a standing position and to support the patient in a standing position.

Another object of the invention is to provide a stand device of the character described wherein the lift mechansim is adapted to be quickly and easily attached to existing stands. The lift can thus be included with the stand as original equipment or provided in kit form for attachment to existing stands.

Yet another object of the invention is to provide a stand device of the character described in which the lift mechanism is sufficiently strong to handle heavy loads without undue difficulty.

A further object of the invention is to provide a device of the character described which is capable of accomodating patients having various heights and weights.

An additional object of the invention is to provide a device of the character described wherein the lift mechanism is constructed to raise and lower the patient in a safe and efficient manner.

A still further object of the invention is to provide a device of the character described which is simple and economical to construct and operate.

Other and further objects of the invention, together with the features of novelty appurtenant thereto, will appear in the course of the following description.

DETAILED DESCRIPTION OF THE INVENTION

In the accompanying drawings which form a part of the specification and are to be read in conjunction therewith and in which like reference numerals are used to indicte like parts in the various views.

Figure 1:
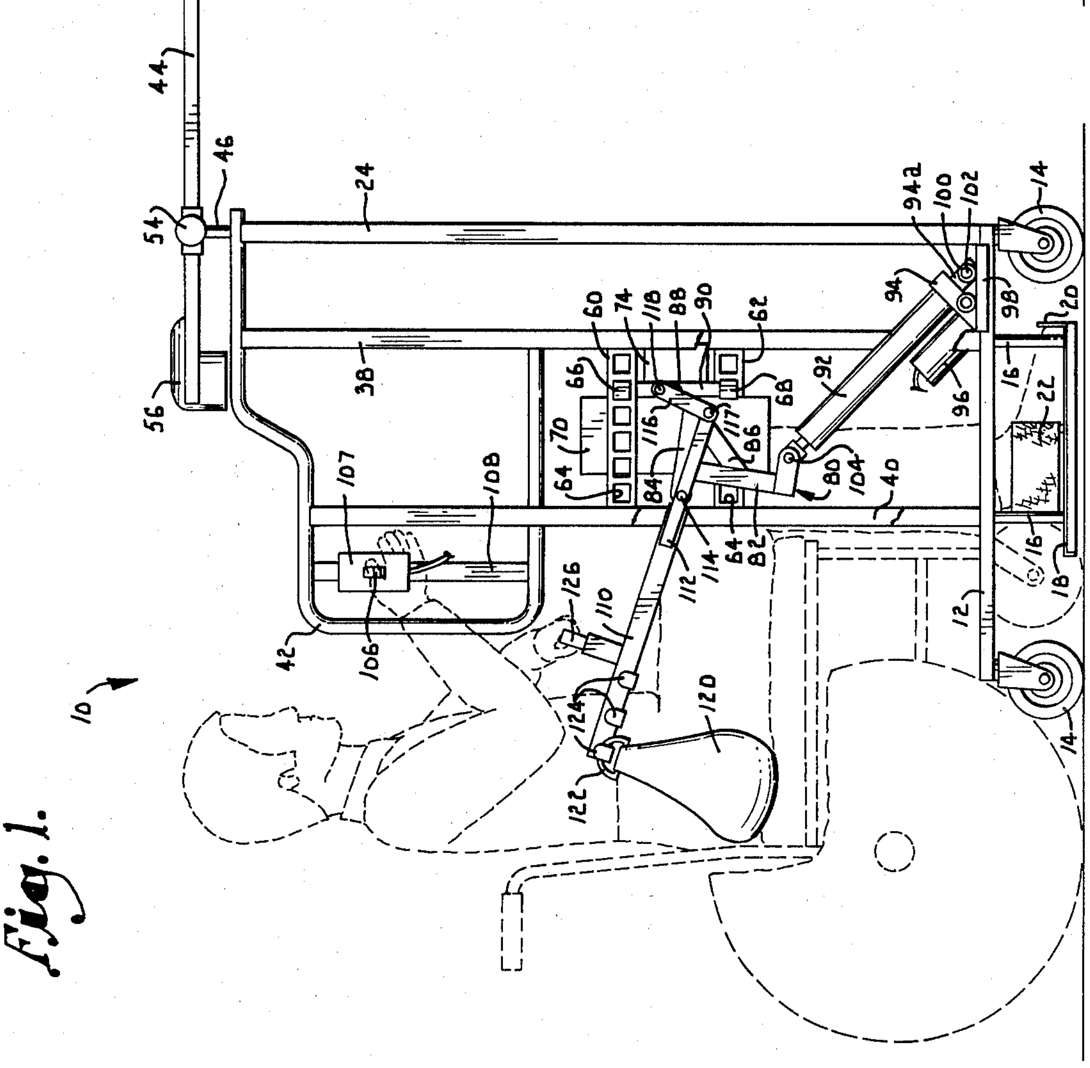
FIG. 1 is a side elevational view of a stand device which is equipped with a lift mechanism constructed according to a preferred embodiment of the present invention, with the lift mechanism lowered and applied to a paraplegic patient shown in broken lines seated in a wheel chair.

Referring now to the drawings in detail, reference numeral 10 generally designates a stand device constructed in accordance with the present invention. The device has an upright frame which includes a pair of horizontal bars 12 each carrying a pair of caster wheels 14 at its opposite ends. A pair of short vertical bars 16 extend downwardly from each horizontal bar 12 and are secured at their lower ends to a horizontal platform 18 which receives the feet of the patient. Platform 18 has a flange 20 on its front edge which serves as a toe piece for contacting the toes of the patient. The platform is also equipped with a pair of adjustable heel straps 22 which receive the heels of the patient.

Figure 3:
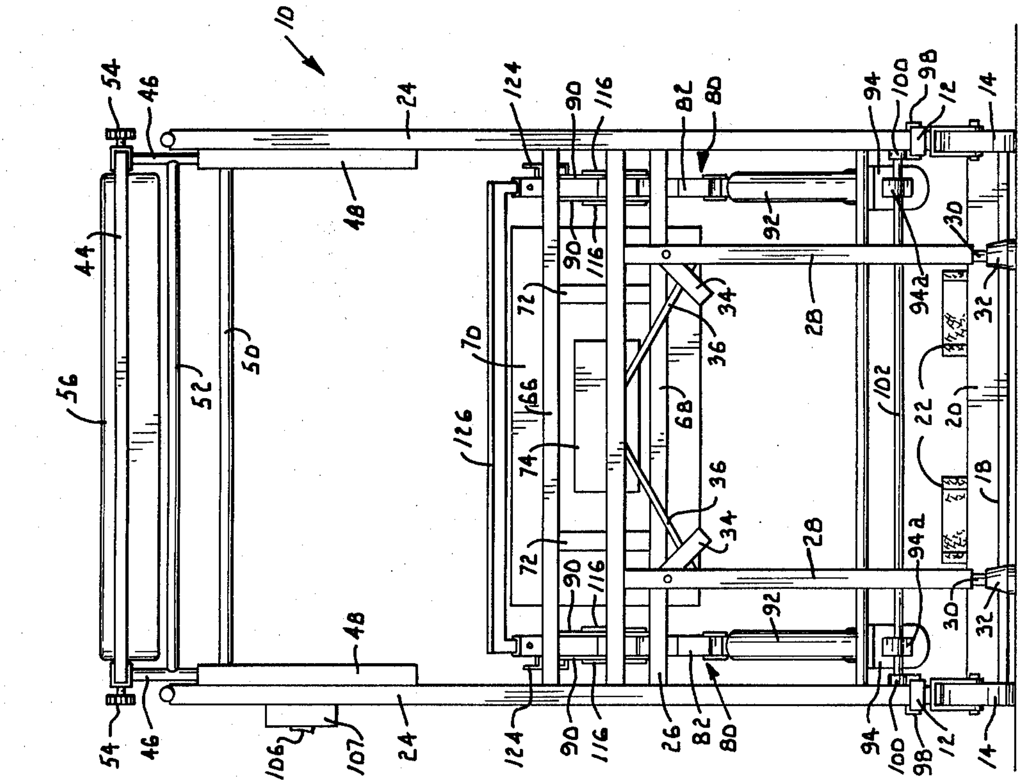
FIG. 3 is a front elevational view of the stand device shown in FIG. 1.

The frame of the stand device further includes a pair of vertical bars 24 which extend upwardly from the forward ends of bars 12 and are interconnected by a horizontal cross bar 26 (FIG. 3). A pair of square tubes 28 extend downwardly from cross bar 26 and slidably receive legs 30*a* carrying pads 32 on their lower ends. Each leg 30 can be extended downwardly such that its pad 32 contacts the floor by activating a lever 34 which is pivoted to tube 28. An actuating rod 36 extends from each lever 34 in order to facilitate pivoting of the lever to extend and retract legs 30.

Additional pairs of vertical bars 38 and 40 extend upwardly from bars 12. A pair of curved push bars 42 are secured to the top ends of bars 24, 38 and 40 and to intermediate portions of bars 38 and 40. A table 44 is mounted on top of a pair of rods 46 which extend downwardly into sleeves 48 secured to the upper portions of bars 24. Sleeves 48 are interconnected by cross bar 50, while the rods 46 are similarly connected by a cross bar 52. The height of table 44 can be adjusted by extending or retracting rods 46 into or out of sleeves 48. The angle of table 44 can also be adjusted by loosening handles 54 and adjusting the inclination of the table prior to again tightening the handles. The back edge of table 44 is equipped with a cushion 56 which is located to contact the chest of a patient standing on platform 18.

Figure 2:
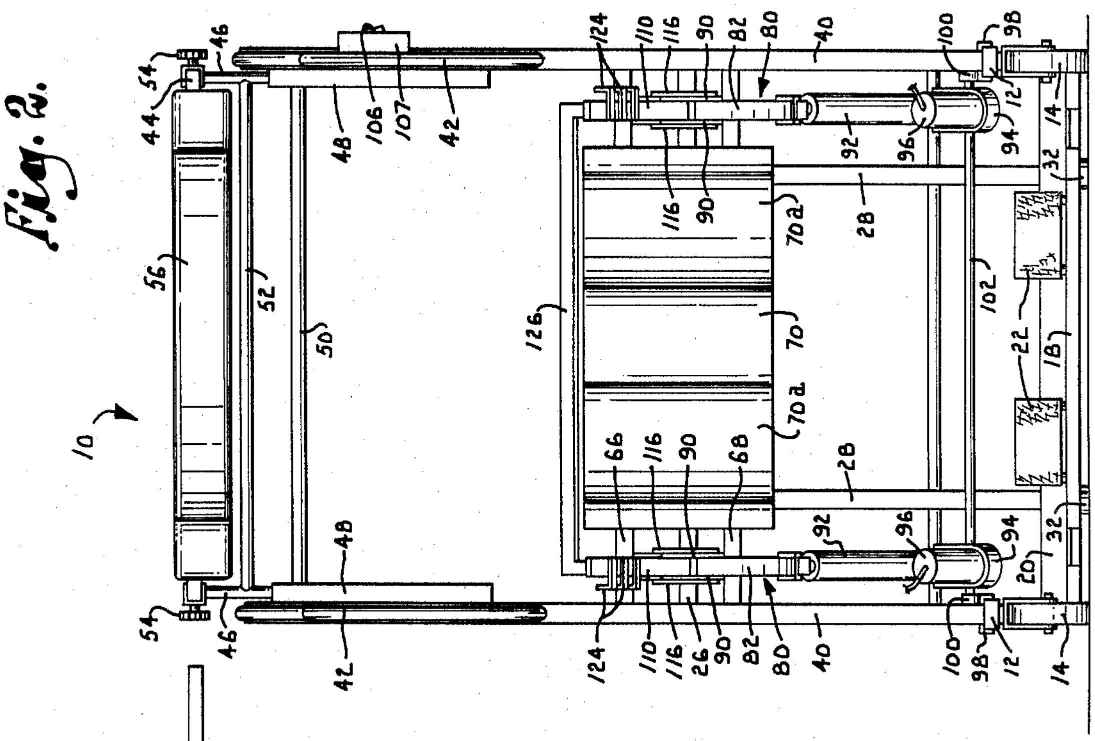
FIG. 2 is a rear elevational view of the stand device shown in FIG. 1.

Upper and lower brackets 60 and 62 extend between intermediate portions of each pair of vertical bars 38 and 40. Each bracket 60 and 62 has a plurality of square openings 64 which are adapted to closely receive the opposite end portions of upper and lower bars 66 and 68 forming part of a bracket to which a knee pad 70 is bolted. A pair of vertical bars 72 (FIG. 3) extend between the upper and lower bars 66 and 68. As best shown in FIG. 2, knee pad 70 is contoured to present a pair of curved recesses 70*a* which receive the knees of a patient standing on the platform 18. Bars 66 and 68 may be pinned to maintain them in openings 64 and may be adjusted toward the front or back of the unit by unpinning the bars and moving them to different openings 64. A rechargable battery (not shown) is carried within a box 74 secured to the front surface of knee pad 70.

Figure 4:
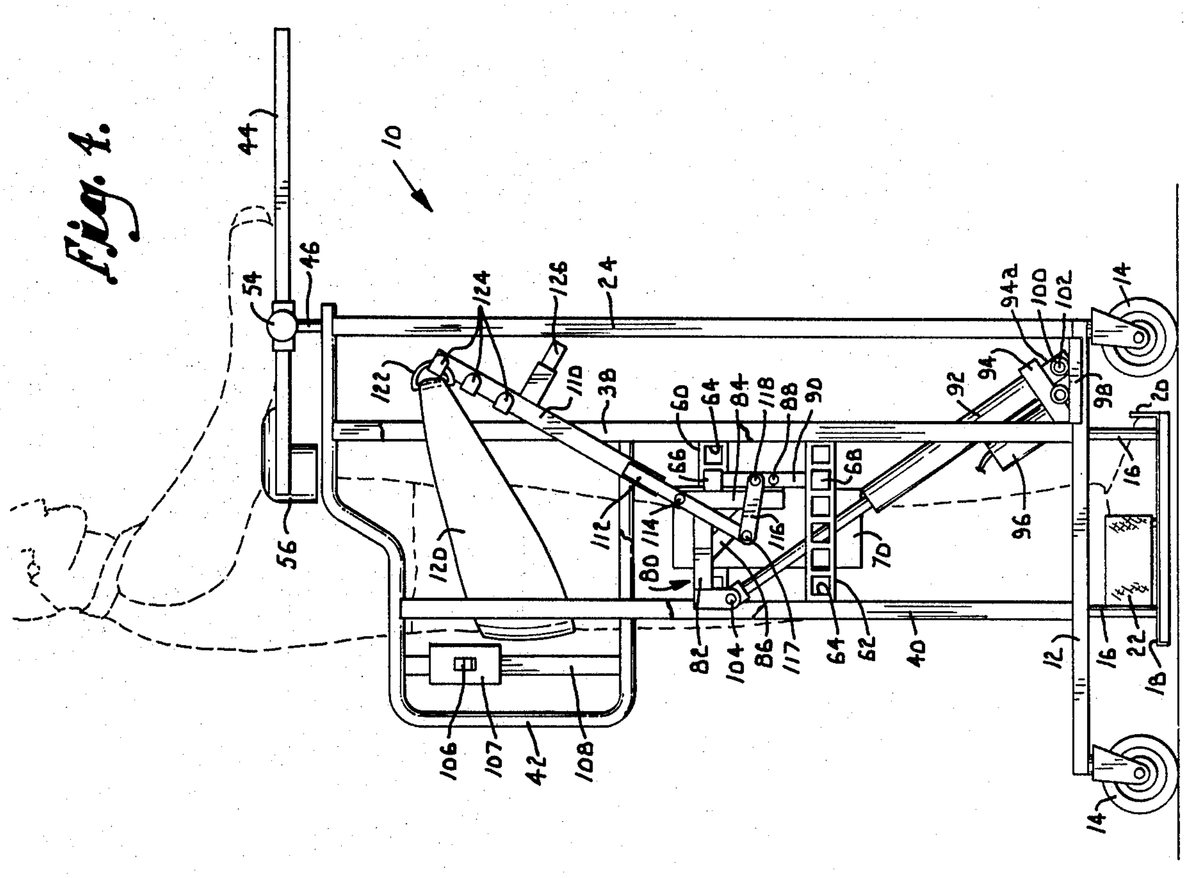
FIG. 4 is a side elevational view similar to FIG. 1, but showing the lift mechanism in its raised position to raise the patient to a standing position.

In accordance with the present invention, the stand device 10 is equipped with a lift mechanism that serves to raise the patient from a wheel chair to a standing position on platform 18. As best shown in FIGS. 1 and 4, the lift mechanism includes a pair of rigid "L" shaped levers 80 each having a rocker arm 82 and a second arm 84 rigidly secured to the upper end of arm 82 and extending perpendicular thereto. A brace 86 angles between arms 82 and 84 to strengthen the lever. The forward end of each arm 84 is pivotally pinned at 88 between a pair of metal brackets 90 extend vertically between the upper and lower bars 66 and 68.

A 12 volt electric actuator 92 is provided for each lever 80. Each actuator 92 is mounted on a base 94. The bases 94 are pivotally mounted to brackets 98 which are secured to the horizontal bars 12 of the frame. Each bracket 98 has a sleeve 100 which receives a cross shaft 102. Shaft 102 also passes through an extension block **94*a* projecing from each base 94, thereby mounting the power units on brackets 98 for pivotal movement about the horizontal axis of shaft 102. The upper or rod end of each cylinder 92 is pivotally pinned at 104 to the lower end of the corresponding rocker arm 82. Electrical power for driving actuators 92 is provided by the battery (not shown) in box 74 under the control of a switch 106. The switch projects from a switch box 107 which is mounted at a convenient location to a bracket 108 secured to one of the push bars 42. The linkage for the lift mechanism includes a pair of parallel lift arms 110. A pair of spaced apart brackets 112 are rigidly secured to each lift arm 110 to form a forward extension thereof. The rearward end of each arm 84 is pivotally pinned at 114 between intermediate portions of the corresponding pair of brackets 112. A pair of short links 116 are pivotally connected at 117 with the forward end of each pair of brackets 112. The opposite or upper ends of links 116 are pivotally pinned at 118 to the respective brackets 90**.

A flexible sling 120 is used to lift the patient to a standing position. Sling 120 carries metal rings 122 on its opposite ends which are adapted to be hooked onto a plurality of tabs 124 projecting from the rearward ends of arms 110. Tabs 124 are spaced along arms 110 in order to accomodate patients of various heights. A spreader bar 126 extends between lift arms 110 and serves as a handle which may be grasped by the patient.

In use of the device, the paraplegic patient is transported in a wheel chair or the like to the position shown in broken lines in FIG. 1. The feet of the patient are positioned on platform 18 with the heels received in heel straps 22 and the toes engaging flange 20. Sling 102 is drawn behind the back of the patient and is positioned beneath the buttocks of the patient in the wheel chair, and the metal rings 122 are hooked onto selected tabs 124. Switch 106 is then actuated by the patient to extend the piston rods of the electric actuators 92.

As actuators 92 slowly extend, the rigid "L" shaped levers 80 are pivoted upwardly about their horizontal pivot connections 88. This carries pivot pins 114 upwardly along an arc centered at pins 88 and raises lift arms 110 from the position of FIG. 1 to the position of FIG. 4. Links 116 are connected with the forward ends of lift arms 110 and with the frame and thus cooperate with the remainder of the linkage to assure that lift arms 110 move properly from the lowered position of FIG. 1 to the raised position of FIG. 4. As the lift arms are raised, sling 120 pulls the patient slowly upwardly to the standing position shown in broken lines in FIG. 4. The sling thereafter supports the patient in the standing position.

The linkage of the lift mechanism is arranged such that lift arms 110 are pivoted through an arc of approximately 90 degrees while levers 80 are pivoted through a somewhat lesser pivot arc, as can be seen by comparing FIG. 1 with FIG. 4. Since the distance between pivot pins 114 and 117 is greater than the distance between pins 117 and 118 and pins 88 and 118 are fixed relative to one another, pin 114 is necessarily closer to pin 118 in the raised position than in the lowered position, and the end result is that lift arms 110 are moved through a greater pivot arc than levers 80. This amplification of the lifting effect imparted to lift arms 110 is significant in that it decreases the extent to which the power cylinders 92 must be extended and retracted in order to raise and lower the patient. In addition to providing an amplification of the lifting effect, the linkage provides sufficient structural strength to withstand even the heaviest loads that are applied to it.

The patient can be wheeled about in the standing position by an attendant pushing on the push arms 42. When the patient is to be lowered to a wheel chair or the like, switch 106 is activated to retract cylinders 92, thereby pivoting levers 80 downwardly to slowly lower arms 110 toward the position shown in FIG. 1. Once the patient has been fully lowered into the wheel chair, rings 122 can be removed from tabs 124, and the stand device 10 may be wheeled away for storage or additional use.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scop of the claims.

Since many possible embodiments may be made of the invention without departing from the scope thereof, it is to be understood that all matter herein set forth or shown in the accompanying drawings is to be interpreted as illustrative and not in a limiting sense.

Having thus described my invention, I claim:

1. A device for assisting a patient to stand in a generally upright position, said device comprising:

a substantially upright frame having a platform for receiving the feet of the patient;

a pair of lift arms mounted to said frame for movement between a raised position and a lowered position;

sling means carried on said lift arms and adapted to be drawn behind the back of the patient when the patient is in a sitting position and said lift arms are in the lowered position, said sling means being raised with said lift arms to raise the patient to an upright standing position on said platform in response to movement of the lift arms to the raised position; and power means for effecting movement of said lift arms between the lowered and raised positions.

2. A device as set forth in claim 1, wherein said sling means has fastening means on opposite ends thereof for connection with said lift arms, said fastening means being releasable from the lift arm at one end of said sling means.

3. A device as set forth in claim 1, including linkage means coupling said lift arms with the frame for movement between the lowered and raised positions, said power means being coupled with said linkage means to activate same for movement of the lift arms.

4. A device as set forth in claim 3, wherein said linkage means includes:

a pair of rigid lever members pivotally coupled with said frame for movement about a generally horizontal pivot axis under the influence of said power means; and means coupling said lift arms with the respective lever members in a manner to pivot said lift arms between the raised and lowered positions in response to pivotal movement of said lever members.

5. A device as set forth in claim 4, wherein said coupling means is arranged to pivot said lift arms through a greater arc than said lever members are pivoted.

6. A device as set forth in claim 3, wherein said linkage means includes:

rigid lever means pivotally coupled with said frame for movement about a generally horizontal pivot axis, said power means being operable to pivot said lever means about said axis;

means pivotally coupling said lift arms with said lever means; and link means having opposite ends pivoted to said frame and to said lift arms in a manner to effect movement of said lift arms between the raised and lowered positions in response to pivoting of said lever means about said axis.

7. A device as set forth in claim 3, wherein said linkage means includes:

a pair of rigid levers each connected with said power means at one end and pivotally coupled with said frame at another end;

means for pivotally coupling said levers with the respective lift arms; and a pair of links each pivotally coupled at one end with said frame and at an opposite end with the corresponding lift arm in a manner to effect movement of said lift arms between the raised and lowered positions in response to pivotal movement of said levers.

8. A device as set forth in claim 7, wherein said power means comprises a pair of actuators mounted on said frame and connected with said levers in a manner to pivot the levers in response to extension and retraction of said actuators.

9. A device as set forth in claim 1, wherein said sling means has opposite ends, and including means for attaching said opposite ends to said lift arms at a plurality of locations along the length thereof.

* * * * *